US009988423B2

(12) United States Patent
Hauser et al.

(10) Patent No.: US 9,988,423 B2
(45) Date of Patent: Jun. 5, 2018

(54) ORGANOGELS AND EMULSIONS FOR BIOLOGICAL AND NON-BIOLOGICAL APPLICATIONS

(71) Applicant: Agency for Science, Technology and Research, Singapore (SG)

(72) Inventors: Charlotte Hauser, Singapore (SG); Archana Mishra, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days. days.

(21) Appl. No.: 14/380,615

(22) PCT Filed: Feb. 22, 2013

(86) PCT No.: PCT/SG2013/000069
§ 371 (c)(1),
(2) Date: Aug. 22, 2014

(87) PCT Pub. No.: WO2013/126017
PCT Pub. Date: Aug. 29, 2013

(65) Prior Publication Data
US 2015/0038428 A1 Feb. 5, 2015

(30) Foreign Application Priority Data
Feb. 22, 2012 (SG) ................ 201201239-9

(51) Int. Cl.
| | | |
|---|---|---|
| A61K 38/00 | (2006.01) |
| A61P 17/00 | (2006.01) |
| A61K 38/08 | (2006.01) |
| A61K 38/06 | (2006.01) |
| A61K 38/07 | (2006.01) |
| C08L 89/00 | (2006.01) |
| C08L 91/00 | (2006.01) |
| C09D 189/00 | (2006.01) |
| C09D 191/00 | (2006.01) |
| C09J 189/00 | (2006.01) |
| C09J 191/00 | (2006.01) |
| H01B 1/00 | (2006.01) |
| H01B 1/12 | (2006.01) |
| A23L 1/05 | (2006.01) |
| A23L 1/06 | (2006.01) |
| C07K 7/06 | (2006.01) |
| A61K 8/64 | (2006.01) |
| C07K 5/083 | (2006.01) |
| C07K 5/062 | (2006.01) |
| A61K 9/06 | (2006.01) |
| A61K 47/34 | (2017.01) |
| A61K 8/04 | (2006.01) |
| A61Q 19/00 | (2006.01) |
| A61K 9/107 | (2006.01) |
| A61K 45/06 | (2006.01) |
| H01L 51/00 | (2006.01) |

(52) U.S. Cl.
CPC ............... *C07K 7/06* (2013.01); *A61K 8/042* (2013.01); *A61K 8/64* (2013.01); *A61K 9/06* (2013.01); *A61K 9/107* (2013.01); *A61K 38/06* (2013.01); *A61K 38/08* (2013.01); *A61K 45/06* (2013.01); *A61K 47/34* (2013.01); *A61Q 19/00* (2013.01); *C07K 5/06034* (2013.01); *C07K 5/0808* (2013.01); *H01L 51/0093* (2013.01); *A61K 2800/10* (2013.01); *A61K 2800/48* (2013.01)

(58) Field of Classification Search
None
See application file for complete search history.

(56) References Cited

U.S. PATENT DOCUMENTS 5,674,642 A * 10/1997 Le .................. C01G 31/00
423/594.17

FOREIGN PATENT DOCUMENTS

| WO | WO 2008/113992 A2 | 9/2008 |
| WO | WO 2010/013555 A1 | 2/2010 |
| WO | WO 2010/147158 A1 | 12/2010 |
| WO | WO 2011/052613 A1 | 5/2011 |
| WO | WO 2011123061 A1 * | 10/2011 ............. A61K 8/042 |
| WO | WO 2013/126017 A1 | 8/2013 |

OTHER PUBLICATIONS

Simmons et al. "Spatial Compartmentalization of Nanoparticles into Strands of a Self-Assembled Organogel" Nano Letters 2:1037-1042. Published 2002.*
Motulsky et al. "Characterization and biocompatibility of organogels based on L-alanine for parenteral drug delivery implants" Biomaterials 26:6242-6253. Published 2005.*
International Search Report and Written Opinion for PCT/SG2013/000069, dated Apr. 19, 2013.
International Preliminary Report on Patentability for PCT/SG2013/000069, dated Sep. 4, 2014.
Supplementary European Search Report for EP 13752241.3, dated Aug. 20, 2015.
Hauser et al., Natural tri- to hexapeptides self-assemble in water to amyloid beta-type fiber aggregates by unexpected alpha-helical intermediate structures. Proc Natl Acad Sci U S A. Jan. 25, 2011;108(4):1361-6. doi: 10.1073/pnas.1014796108. Epub Jan. 4, 2011.
Lakshmanan et al., Ultrasmall peptides self-assemble into diverse nanostructures: morphological evaluation and potential implications. Int J Mol Sci. 2011;12(9):5736-46. doi: 10.3390/ijms12095736. Epub Sep. 7, 2011.
Japanese Notice of Reasons for Rejection for Japanese Application No. 2014-558713 dated Oct. 25, 2016.
Examination Report for European Application No. 13752241.3, dated Mar. 23, 2017.

* cited by examiner

Primary Examiner — James H Alstrum-Acevedo
Assistant Examiner — Zachary J Miknis
(74) Attorney, Agent, or Firm — Wolf, Greenfield & Sacks, P.C.

(57) ABSTRACT

The present invention relates to organogels and emulsions based on ultrasmall self-assembling peptides. It further relates to methods for producing such organogels and emulsions as well as to the use of the organogels and emulsions in biological and non-biological applications.

11 Claims, 12 Drawing Sheets

A

| Solvent | Trimer | | Hexamer |
|---|---|---|---|
| | Ac-IVW-COOH(L) | Ac-IVF-COOH(L) | Ac-LIVAGF-COOH (L) |
| Acetonitrile | S | G | A |
| Acetone | G | G | G (partial) |
| Ethyl acetate | G | G | A |
| Chloroform | A | G | A |
| Toluene | A | A | A |

A - Aggregated; S - Suspension; G - Gelation

B

Trimer    Hexamer

B

C

| Sr. No. | Ethyl acetate: Chloroform | Observation (gels) |
|---|---|---|
| 1 | 5:5 | Opaque |
| 2 | 6:4 | Opaque |
| 3 | 7:3 | Semi Opaque |
| 4 | 8:2 | Translucent and stable in comparison to above |
| 5 | 9:1 | Semi opaque and stable in comparison to above |

SEQUENCE LISTING

<160> NUMBER OF SEQ ID NOS: 48

<210> SEQ ID NO 1
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 1

Leu Ile Val Ala Gly
1               5

<210> SEQ ID NO 2
<211> LENGTH: 5
<212> TYPE: PRT
<213> ORGANISM: Artificial Sequence

```
<220> FEATURE:
<223> OTHER INFORMATION: Synthetic Peptide

<400> SEQUENCE: 2

Ile Leu Val Ala Gly
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 3

Leu Ile Val Ala Ala
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 4

Leu Ala Val Ala Gly
1               5

<210> SEQ ID NO 5
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 5

Ile Val Ala Gly
1

<210> SEQ ID NO 6
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 6

Leu Ile Val Ala
1

<210> SEQ ID NO 7
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 7

Leu Ile Val Gly
1

<210> SEQ ID NO 8
<211> LENGTH: 3
<212> TYPE: PRT
<213> ORGANISM: Artificial Sequence
```

```
<220> FEATURE:
<223> OTHER INFORMATION: Synthetic Peptide

<400> SEQUENCE: 8

Ile Val Ala
1

<210> SEQ ID NO 9
<211> LENGTH: 2
<212> TYPE: PRT
<213> ORGANISM: Artificial Sequence
<220> FEATURE:
<223> OTHER INFORMATION: Synthetic Peptide

<400> SEQUENCE: 9

Ile Val
1

<210> SEQ ID NO 10
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 10

Leu Ile Val Ala Gly Cys
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 11

Leu Ile Val Ala Gly Asp
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 12

Leu Ile Val Ala Gly Phe
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 13

Leu Ile Val Ala Gly Trp
1               5

<210> SEQ ID NO 14
<211> LENGTH: 6
<212> TYPE: PRT
<213> ORGANISM: Artificial Sequence
```

```
<220> FEATURE:
<223> OTHER INFORMATION: Synthetic Peptide

<400> SEQUENCE: 14

Ile Leu Val Ala Gly Asp
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 15

Leu Ile Val Ala Ala Asp
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 16

Leu Ala Val Ala Gly Asp
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 17

Ala Ile Val Ala Gly Asp
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 18

Leu Ile Val Ala Gly Glu
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 19

Leu Ile Val Ala Gly Lys
1               5

<210> SEQ ID NO 20
<211> LENGTH: 6
<212> TYPE: PRT
<213> ORGANISM: Artificial Sequence
```

```
<220> FEATURE:
<223> OTHER INFORMATION: Synthetic Peptide

<400> SEQUENCE: 20

Leu Ile Val Ala Gly Ser
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 21

Ile Leu Val Ala Gly Ser
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 22

Ala Ile Val Ala Gly Ser
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 23

Leu Ile Val Ala Gly Thr
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 24

Ala Ile Val Ala Gly Thr
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 25

Leu Ile Val Ala Asp
1               5

<210> SEQ ID NO 26
<211> LENGTH: 5
<212> TYPE: PRT
<213> ORGANISM: Artificial Sequence
```

```
<220> FEATURE:
<223> OTHER INFORMATION: Synthetic Peptide

<400> SEQUENCE: 26

Leu Ile Val Gly Asp
1               5

<210> SEQ ID NO 27
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 27

Ile Val Ala Asp
1

<210> SEQ ID NO 28
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 28

Ile Ile Ile Asp
1

<210> SEQ ID NO 29
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 29

Ile Ile Ile Lys
1

<210> SEQ ID NO 30
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 30

Ile Val Asp
1

<210> SEQ ID NO 31
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 31

Ile Val Phe
1

<210> SEQ ID NO 32
<211> LENGTH: 3
<212> TYPE: PRT
<213> ORGANISM: Artificial Sequence
```

```
<220> FEATURE:
<223> OTHER INFORMATION: Synthetic Peptide

<400> SEQUENCE: 32

Ile Val Trp
1

<210> SEQ ID NO 33
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 33

Ile Ile Asp
1

<210> SEQ ID NO 34
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 34

Leu Val Glu
1

<210> SEQ ID NO 35
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 35

Ile Val Glu
1

<210> SEQ ID NO 36
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 36

Leu Val Asp
1

<210> SEQ ID NO 37
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 37

Val Ile Glu
1

<210> SEQ ID NO 38
<211> LENGTH: 3
<212> TYPE: PRT
<213> ORGANISM: Artificial Sequence
```

```
<220> FEATURE:
<223> OTHER INFORMATION: Synthetic Peptide

<400> SEQUENCE: 38

Val Ile Asp
1

<210> SEQ ID NO 39
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 39

Val Leu Asp
1

<210> SEQ ID NO 40
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 40

Val Leu Glu
1

<210> SEQ ID NO 41
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 41

Leu Leu Glu
1

<210> SEQ ID NO 42
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 42

Leu Leu Asp
1

<210> SEQ ID NO 43
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 43

Ile Ile Glu
1

<210> SEQ ID NO 44
<211> LENGTH: 2
<212> TYPE: PRT
<213> ORGANISM: Artificial Sequence
```

```
<220> FEATURE:
<223> OTHER INFORMATION: Synthetic Peptide

<400> SEQUENCE: 44

Ile Asp
1

<210> SEQ ID NO 45
<211> LENGTH: 2
<212> TYPE: PRT
<213> ORGANISM: Artificial Sequence
<220> FEATURE:
<223> OTHER INFORMATION: Synthetic Peptide

<400> SEQUENCE: 45

Ile Glu
1

<210> SEQ ID NO 46
<211> LENGTH: 2
<212> TYPE: PRT
<213> ORGANISM: Artificial Sequence
<220> FEATURE:
<223> OTHER INFORMATION: Synthetic Peptide

<400> SEQUENCE: 46

Ile Trp
1

<210> SEQ ID NO 47
<211> LENGTH: 2
<212> TYPE: PRT
<213> ORGANISM: Artificial Sequence
<220> FEATURE:
<223> OTHER INFORMATION: Synthetic Peptide

<400> SEQUENCE: 47

Ile Phe
1

<210> SEQ ID NO 48
<211> LENGTH: 2
<212> TYPE: PRT
<213> ORGANISM: Artificial Sequence
<220> FEATURE:
<223> OTHER INFORMATION: Synthetic Peptide

<400> SEQUENCE: 48

Ile Tyr
1
```

ORGANOGELS AND EMULSIONS FOR BIOLOGICAL AND NON-BIOLOGICAL APPLICATIONS

RELATED APPLICATIONS

This application is a U.S. National Stage application under 35 U.S.C. § 371 based on International Application No. PCT/SG2013/000069, filed Feb. 22, 2013, which claims priority to Singapore Patent Application No. 201201239-9, filed Feb. 22, 2012, each of which is incorporated by reference herein in its entirety.

FIELD OF INVENTION

The present invention relates to organogels and emulsions based on ultrasmall self-assembling peptides. It further relates to methods for producing such organogels and emulsions as well as to the use of the organogels and emulsions in biological and non-biological applications.

BACKGROUND

Organogels are composed of a liquid organic phase that is immobilized in a three-dimensional scaffold made from self-assembled or cross-linked gelators. To date, the formation of reported peptide organogels requires complex methodologies to fabricate scaffolds, for example, use of oxidized glutathione and its derivatives for organogelation by heating (Lyon R P and Atkins W M, J. Am. Chem. Soc. 2001; 123(19):4408-4413) or use of co-solvents such as 1,1,1,3,3,3-hexafluoro-2-propanol to formulate diphenylalanine-based organogels (Yan X et al., Chem. Mat. 2008; 20(4): 1522-1526). Hence, a more facile to handle and cheap technology would be a clear advantage. There is also a demand for gelators that are of low-cost, easy to synthesize, stable and Versatile to produce organogels in different solvent systems.

Accordingly, it was an object of the present invention to provide new types of organogel and/or emulsion systems that have the above properties. Furthermore; the organogels and/or emulsions should exhibit high versatility, good material properties and, if necessary, biocompatibility so that they can be used both in biological and non-biological applications.

DISCLOSURE OF INVENTION

The objects of the present invention are solved by an organogel comprising an organic solvent and a peptide having the general formula

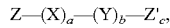

wherein
Z is an N-terminal protecting group;
X is, at each occurrence, independently selected from the group consisting of aliphatic amino acids and aliphatic amino acid derivatives;
Y is selected from the group consisting of polar amino acids, polar amino acid derivatives, aromatic amino acids and aromatic amino acid derivatives;
Z' is a C-terminal protecting group;
a is an integer selected from 1 to 6, preferably 1 to 5;
b is 0, 1 or 2, preferably 1; and
c is 0 or 1.

In one embodiment, said organic solvent is selected from polar organic solvents, preferably selected from the group consisting of alcohols, such as methanol, ethanol, propanol, isopropanol, isopentanol and 2-methoxyethanol, ketones, such as acetone, methylethyl ketone, methyl n-propyl ketone, methyl isopropyl ketone and methyl isoamyl ketone, ethers, such as ethylene glycol monobutyl ether and propylene glycol monomethyl ether, methyl acetate, ethyl acetate, propyl acetate, n-butyl acetate, chloroform, acetonitrile, glycerol, dimethyl sulfoxide, N,N-dimethyl formamide, tetrahydrofuran, pyridine, 1,4-dioxane, dimethyl acetamide, N-methylpyrrolidone, propylene carbonate and mixtures thereof.

In one embodiment, said organic solvent is selected from non-polar organic solvents, preferably selected from the group consisting of benzene, chlorobenzene, o-dichlorobenzene, toluene, o-xylene, dichloromethane, 1,1,2-trichlorotrifluoroethane, pentane, cyclopentane, hexane, cyclohexane, heptane, iso octane, diethylether, petroleum ether, pyridine, carbon tetrachloride, fatty acids, fatty acid esters and mixtures thereof.

In one embodiment, said organic solvent is selected from oils, preferably selected from the group consisting of vegetable oils, essential oils, petrochemical oils, synthetic oils and mixtures thereof. When oils are used, said organic solvent may also be referred to as lipophilic solvent.

In one embodiment, said organic solvent is a mixture of at least one polar or non-polar organic solvent as defined above and at least one oil as defined above.

In one embodiment, said organic solvent is a physiologically acceptable solvent.

In one embodiment, said aliphatic amino acids and aliphatic amino acid derivatives, said polar amino acids and polar amino acid derivatives, and said aromatic amino acids and aromatic amino acid derivatives are either D-amino acids or L-amino acids.

In one embodiment, said aliphatic amino acids are selected from the group consisting of alanine (Ala, A), homoallylglycine, homopropargylglycine, isoleucine (Ile, I), norleucine, leucine (Leu, L), valine (Val, V) and glycine (Gly, G), preferably from the group consisting of alanine (Ala, A), isoleucine (Ile, I), leucine (Leu, L), valine (Val, V) and glycine (Gly, G).

In one embodiment, all or a portion of said aliphatic amino acids are arranged in an order of decreasing amino acid size in the direction from N- to C-terminus, wherein the size of the aliphatic amino acids is defined as I=L>V>A>G.

In one embodiment, said aliphatic amino acids arranged in an order of decreasing amino acid size have a sequence selected from LIVAG (SEQ ID NO: 1), ILVAG (SEQ ID NO: 2), LIVAA (SEQ ID NO: 3), LAVAG (SEQ ID NO: 4), IVAG (SEQ ID NO: 5); LIVA (SEQ ID NO: 6), LIVG (SEQ ID NO: 7), IVA (SEQ ID NO: 8) and IV (SEQ ID NO: 9), wherein, optionally, there is an A preceding such sequence at the N-terminus.

In one embodiment, said polar amino acids and polar amino acid derivatives acid have a polar group which is independently selected from a hydroxyl, an ether, a carboxyl, an imido, an amido, an ester, an amino, a guanidino, a thio, a thioether, a seleno, and a telluro group.

In one embodiment, said polar amino acids are selected from the group consisting of aspartic acid (Asp, D), asparagine (Asn, N), glutamic acid (Glu, E), glutamine (Gln, Q), 5-N-ethyl-glutamine (theanine), citrulline, thio-citrulline, cysteine (Cys, C), homocysteine, methionine (Met, M), ethionine, selenomethionine, telluromethionine, serine (Ser, S), homoserine, arginine (Arg, R), homoarginine, ornithine (Orn), threonine (Thr, T), L-Dopa, tryptophan (Trp, W), thyroxine, allo-threonine, lysine (Lys, K), 2,4-diaminobutyric acid (Dab), 2,3-diaminopropionic acid (Dap), N(6)-carboxymethyllysine, tyrosine (Tyr, Y) and histidine (His, H). In one embodiment, said polar amino acids are selected from the group consisting of aspartic acid (Asp, D), glutamic acid (Glu, E), serine (Ser, S), threonine (Thr, T), lysine (Lys, K), ornithine (Orn), 2,4-diaminobutyric acid (Dab) and 2,3-diaminopropionic acid (Dap). In one embodiment, said polar amino acids are selected from the group consisting of aspartic acid (Asp, D) and glutamic acid (Glu, E).

In one embodiment, said aromatic amino acids are selected from the group consisting of phenylalanine (Phe, F), tryptophan (Trp, W), tyrosine (Tyr, Y), histidine (His, H) and L-Dopa.

In one embodiment, $(X)_a$—$(Y)_b$ has a sequence selected from the group consisting of LIVAGC (SEQ ID NO: 10), LIVAGD (SEQ ID NO: 11), LIVAGF (SEQ ID NO: 12), LIVAGW (SEQ ID NO: 13), ILVAGD (SEQ ID NO: 14), LIVAAD (SEQ ID NO: 15), LAVAGD (SEQ ID NO: 16), AIVAGD (SEQ ID NO: 17), LIVAGE (SEQ ID NO: 18), LIVAGK (SEQ ID NO: 19), LIVAGS (SEQ ID NO: 20), ILVAGS (SEQ ID NO: 21), AIVAGS (SEQ ID NO: 22), LIVAGT (SEQ ID NO: 23), AIVAGT (SEQ ID NO: 24), LIVAD (SEQ ID NO: 25), LIVGD (SEQ ID NO: 26), IVAD (SEQ ID NO: 27), IIID (SEQ ID NO: 28), IIIK (SEQ ID NO: 29), IVD (SEQ ID NO: 30), IVF (SEQ ID NO: 31), IVW (SEQ ID NO: 32), IID (SEQ ID NO: 33), LVE (SEQ ID NO: 34), IVE (SEQ ID NO: 35), LVD (SEQ ID NO: 36), VIE (SEQ ID NO: 37), VID (SEQ ID NO: 38), VLD (SEQ ID NO: 39), VLE (SEQ ID NO: 40), LLE (SEQ ID NO: 41), LLD (SEQ ID NO: 42), IIE (SEQ ID NO: 43), ID (SEQ ID NO: 44), IE (SEQ ID NO: 45), IW (SEQ ID NO: 46), IF (SEQ ID NO: 47) and IY (SEQ ID NO: 48).

In one embodiment, the C-terminal amino acid of the peptide is selected from the group consisting of a lysine (K), an ornithine (Orn), a 2,4-diaminobutyric acid (Dab) and a 2,3-diaminopropionic acid (Dap).

In one embodiment, said N-terminal protecting group has the general formula —C(O)—R, wherein R is selected from the group consisting of H, alkyl and substituted alkyl.

In one embodiment, R is selected from the group consisting of methyl, ethyl, propyl, isopropyl, butyl and isobutyl.

In one embodiment, said N-terminal protecting group is an acetyl group.

In one embodiment, the C-terminus of said peptide is amidated, wherein, preferably, the C-terminus has the formula —CONHR, with R being selected from the group consisting of H, alkyl and substituted alkyl.

In one embodiment, the C-terminus of said peptide is esterified, wherein, preferably, the C-terminus has the formula —$CO_2R$, with R being selected from the group consisting of alkyls and substituted alkyls.

In one embodiment, R is selected from the group consisting of methyl, ethyl, propyl, isopropyl, butyl and isobutyl.

In one embodiment, the C-terminal amino acid of said peptide is a peptidomimetic amino acid, wherein, preferably, the C1 carboxyl group of said peptidomimetic amino acid is replaced with an alcohol, ester, aldehyde or ketone group.

In case b is 0, c is preferably 0, i.e. the peptide does not carry a C-terminal protecting group.

In one embodiment, a is an integer selected from 1 to 5, preferably 2 to 5, and wherein, preferably, said aliphatic amino acids and aliphatic amino acid derivatives exhibit an overall decrease in hydrophobicity from the N-terminus to the C-terminus of said peptide.

In one embodiment, said peptide is present at a concentration in the range of from 0.1% to 30% (w/w), preferably 0.1% to 20% (w/w), more preferably 0.1% to 10% (w/w), more preferably 0.1% to 5% (w/w), even more preferably 0.1% to 3% (w/w), with respect to the total weight of said organogel.

In one embodiment, said organogel has a tan δ of less than 1, preferably less than 0.5.

In one embodiment, said organogel further comprises at least one additional substance.

In one embodiment, said at least one additional substance is encapsulated by said organogel, immobilized in the bulk phase of said organogel or conjugated to said peptide.

In one embodiment, said at least one additional substance is a bioactive agent, wherein said bioactive agent is preferably selected from the group consisting of nucleic acids, (poly)peptides, virus particles, oligosaccharides, polysaccharides, vitamins, sialic acids, antigens, vaccines, drugs, prodrugs and other organic or inorganic bioactive compounds.

In one embodiment, said bioactive agent is selected from the group comprising haemostatic agents, antibiotics, antimicrobial agents, anti-fungal agents, anti-inflammatory agents, analgesics, anti-coagulants, antibodies, antigens, growth factors and cytokines.

In one embodiment, said at least one additional substance is selected from the group consisting of dyes, pigments, quantum dot nanoparticles and other nanoparticles, preferably metal or semiconductor nanoparticles.

The objects of the present invention are also solved by a method of producing an organogel as defined above, said method comprising the step of dissolving a peptide as defined above in an organic solvent as defined above.

In one embodiment, said method further comprises at least one of the following steps:
  heating said peptide in said organic solvent, preferably to a temperature in the range of from 30 to 50° C.;
  sonicating said peptide in said organic solvent.

The objects of the present invention are also solved by the use of a peptide as defined above as gelator in an organogel.

The objects of the present invention are also solved by the use of an organogel as defined above in a pharmaceutical formulation, a cosmetic or personal care product, a food product or a device.

The objects of the present invention are also solved by a pharmaceutical formulation comprising an organogel as defined above. In one embodiment, said pharmaceutical formulation is a controlled or sustained release pharmaceutical formulation. In one embodiment, the pharmaceutical composition further comprises a bioactive agent as defined above. In one embodiment, the pharmaceutical composition further comprises a pharmaceutically acceptable carrier. In one embodiment, the pharmaceutical composition is applied topically.

The objects of the present invention are also solved by a cosmetic or personal care product comprising an organogel as defined above. In one embodiment, the cosmetic product is applied topically.

The objects of the present invention are also solved by a food product comprising an organogel as defined above.

The objects of the present invention are also solved by a device comprising an organogel as defined above. In one embodiment, said device is a sensor device. In one embodiment, said device is an electronic device.

The objects of the present invention are also solved by an emulsion comprising an organic solvent, a polar solvent, preferably an aqueous solution, and a peptide having the general formula

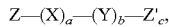

$$Z-(X)_a-(Y)_b-Z'_c,$$

wherein
Z is an N-terminal protecting group;
X is, at each occurrence, independently selected from the group consisting of aliphatic amino acids and aliphatic amino acid derivatives;
Y is selected from the group consisting of polar amino acids, polar amino acid derivatives, aromatic amino acids and aromatic amino acid derivatives, preferably polar amino acids and polar amino acid derivatives;
Z' is a C-terminal protecting group;
a is an integer selected from 1 to 6, preferably 1 to 5;
b is 0, 1 or 2, preferably 1; and
c is 0 or 1.

In one embodiment, said organic solvent is selected from polar organic solvents, preferably selected from the group consisting of alcohols, such as methanol, ethanol, propanol, isopropanol, isopentanol and 2-methoxyethanol, ketones, such as acetone, methylethyl ketone, methyl n-propyl ketone, methyl isopropyl ketone and methyl isoamyl ketone, ethers, such as ethylene glycol monobutyl ether and propylene glycol monomethyl ether, methyl acetate, ethyl acetate, propyl acetate, n-butyl acetate, chloroform, acetonitrile, glycerol, dimethyl sulfoxide, N,N-dimethyl formamide, tetrahydrofuran, pyridine, 1,4-dioxane, dimethyl acetamide, N-methylpyrrolidone, propylene carbonate and mixtures thereof.

In one embodiment, said organic solvent is selected from non-polar organic solvents, preferably selected from the group consisting of benzene, chlorobenzene, o-dichlorobenzene, toluene, o-xylene, dichloromethane, 1,1,2-trichlorotrifluoroethane, pentane, cyclopentane, hexane, cyclohexane, heptane, iso octane, diethylether, petroleum ether, pyridine, carbon tetrachloride, fatty acids, fatty acid esters and mixtures thereof.

In one embodiment, said organic solvent is selected from oils, preferably selected from the group consisting of vegetable oils, essential oils, petrochemical oils, synthetic oils and mixtures thereof. When oils are used, said organic solvent may also be referred to as lipophilic solvent.

In one embodiment, said organic solvent is a mixture of at least one polar or non-polar organic solvent as defined above and at least one oil as defined above.

In one embodiment, said organic solvent is a physiologically acceptable solvent.

In one embodiment, said aliphatic amino acids are selected from the group consisting of alanine (Ala, A), homoallylglycine, homopropargylglycine, isoleucine (Ile, I), norleucine, leucine (Leu, L), valine (Val, V) and glycine (Gly, G), preferably from the group consisting of alanine (Ala, A), isoleucine (Ile, I), leucine (Leu, L), valine (Val, V) and glycine (Gly, G).

In one embodiment, all or a portion of said aliphatic amino acids are arranged in an order of decreasing amino acid size in the direction from N- to C-terminus, wherein the size of the aliphatic amino acids is defined as I=L>V>A>G.

In one embodiment, said aliphatic amino acids arranged in an order of decreasing amino acid size have a sequence selected from LIVAG (SEQ ID NO: 1), ILVAG (SEQ ID NO: 2), LIVAA (SEQ ID NO: 3), LAVAG (SEQ ID NO: 4), NAG (SEQ ID NO: 5); LIVA (SEQ ID NO: 6), LIVG (SEQ ID NO: 7), IVA (SEQ ID NO: 8) and IV (SEQ ID NO: 9), wherein, optionally, there is an A preceding such sequence at the N-terminus.

In one embodiment, said polar amino acids and polar amino acid derivatives acid have a polar group which is independently selected from a hydroxyl, an ether, a carboxyl, an imido, an amido, an ester, an amino, a guanidino, a thio, a thioether, a seleno, and a telluro group.

In one embodiment, said polar amino acids are selected from the group consisting of aspartic acid (Asp, D), asparagine (Asn, N), glutamic acid (Glu, E), glutamine (Gln, Q), 5-N-ethyl-glutamine (theanine), citrulline, thio-citrulline, cysteine (Cys, C), homocysteine, methionine (Met, M), ethionine, selenomethionine, telluromethionine, serine (Ser, S), homoserine, arginine (Arg, R), homoarginine, ornithine (Orn), threonine (Thr, T), L-Dopa, tryptophan (Trp, W), thyroxine, allo-threonine, lysine (Lys, K), 2,4-diaminobutyric acid (Dab), 2,3-diaminopropionic acid (Dap), N(6)-carboxymethyllysine, tyrosine (Tyr, Y) and histidine (His, H). In one embodiment, said polar amino acids are selected from the group consisting of aspartic acid (Asp, D), glutamic acid (Glu, E), serine (Ser, S), threonine (Thr, T), lysine (Lys, K), ornithine (Orn), 2,4-diaminobutyric acid (Dab) and 2,3-diaminopropionic acid (Dap). In one embodiment, said polar amino acids are selected from the group consisting of aspartic acid (Asp, D) and glutamic acid (Glu, E).

In one embodiment, said aromatic amino acids are selected from the group consisting of phenylalanine (Phe, F), tryptophan (Trp, W), tyrosine (Tyr, Y), histidine (His, H) and L-Dopa.

In one embodiment, $(X)_a-(Y)_b$ has a sequence selected from the group consisting of LIVAGC (SEQ ID NO: 10), LIVAGD (SEQ ID NO: 11), LIVAGF (SEQ ID NO: 12), LIVAGW (SEQ ID NO: 13), ILVAGD (SEQ ID NO: 14), LIVAAD (SEQ ID NO: 15), LAVAGD (SEQ ID NO: 16), AIVAGD (SEQ ID NO: 17), LIVAGE (SEQ ID NO: 18), LIVAGK (SEQ ID NO: 19), LIVAGS (SEQ ID NO: 20), ILVAGS (SEQ ID NO: 21), AIVAGS (SEQ ID NO: 22), LIVAGT (SEQ ID NO: 23), AIVAGT (SEQ ID NO: 24), LIVAD (SEQ ID NO: 25), LIVGD (SEQ ID NO: 26), IVAD (SEQ ID NO: 27), IIID (SEQ ID NO: 28), IIIK (SEQ ID NO: 29), IVD (SEQ ID NO: 30), IVF (SEQ ID NO: 31), IVW (SEQ ID NO: 32), IID (SEQ ID NO: 33), LVE (SEQ ID NO: 34), IVE (SEQ ID NO: 35), LVD (SEQ ID NO: 36), VIE (SEQ ID NO: 37), VID (SEQ ID NO: 38), VLD (SEQ ID NO: 39), VLE (SEQ ID NO: 40), LLE (SEQ ID NO: 41), LLD (SEQ ID NO: 42), IIE (SEQ ID NO: 43), ID (SEQ ID NO: 44), IE (SEQ ID NO: 45), IW (SEQ ID NO: 46), IF (SEQ ID NO: 47) and IY (SEQ ID NO: 48).

In one embodiment, the C-terminal amino acid of the peptide is selected from the group consisting of a lysine (K), an ornithine (Orn), a 2,4-diaminobutyric acid (Dab) and a 2,3-diaminopropionic acid (Dap).

In one embodiment, said N-terminal protecting group has the general formula —C(O)—R, wherein R is selected from the group consisting of H, alkyl and substituted alkyl.

In one embodiment, R is selected from the group consisting of methyl, ethyl, propyl, isopropyl, butyl and isobutyl.

In one embodiment, said N-terminal protecting group is an acetyl group.

In one embodiment, the C-terminus of said peptide is amidated, wherein, preferably, the C-terminus has the formula —CONHR, with R being selected from the group consisting of H, alkyl and substituted alkyl.

In one embodiment, the C-terminus of said peptide is esterified, wherein, preferably, the C-terminus has the formula —$CO_2R$, with R being selected from the group consisting of alkyls and substituted alkyls.

In one embodiment, R is selected from the group consisting of methyl, ethyl, propyl, isopropyl, butyl and isobutyl.

In one embodiment, the C-terminal amino acid of said peptide is a peptidomimetic amino acid, wherein, preferably, the C1 carboxyl group of said peptidomimetic amino acid is replaced with an alcohol, ester, aldehyde or ketone group.

In case b is 0, c is preferably 0, i.e. the peptide does not carry a C-terminal protecting group.

In one embodiment, a is an integer selected from 1 to 5, preferably 2 to 5, and Wherein, preferably, said aliphatic amino acids and aliphatic amino acid derivatives exhibit an overall decrease in hydrophobicity from the N-terminus to the C-terminus of said peptide.

In one embodiment, said peptide is present at a concentration in the range of from 0.1% to 30% (w/v), preferably 0.1% to 20% (w/v), more preferably 0.1% to 10% (w/v), more preferably 0.1% to 5% (w/v), even more preferably 0.1% to 3% (w/v), with respect to the total volume of said emulsion.

In one embodiment, said emulsion further comprises at least one additional substance.

In one embodiment, said additional substance is a bioactive agent, wherein said bioactive agent is preferably selected from the group consisting of nucleic acids, (poly) peptides, virus particles, oligosaccharides, polysaccharides, vitamins, sialic acids, antigens, vaccines, drugs, prodrugs and other organic or inorganic bioactive compounds.

In one embodiment, said bioactive agent is selected from the group comprising haemostatic agents, antibiotics, antimicrobial agents, anti-fungal agents, anti-inflammatory agents, analgesics, anti-coagulants, antibodies, antigens, growth factors and cytokines.

In one embodiment, said additional substance is a dye, opacifier or pigment.

In one embodiment, said additional substance is a wax, such as beeswax and carnauba wax.

The objects of the present invention are also solved by a method of producing an emulsion as defined above, said method comprising the step of dissolving a peptide as defined above in a mixture of a polar solvent, preferably an aqueous solution, and an organic solvent as defined above.

In one embodiment, said method further comprises at least one of the following steps:
sonicating said peptide in said mixture;
homogenizing said peptide in said mixture;
phase separation coacervation and/or precipitation and/or use of a co-solvent with said peptide in said mixture.

In one embodiment, said aqueous solution is water. In one embodiment, said organic solvent is an oil.

The objects of the present invention are also solved by the use of a peptide as defined above as an emulsifier. In one embodiment, said peptide forms micelles.

In one embodiment of the emulsion as defined above, said at least one additional substance as defined above is entrapped in micelles formed by said peptide.

The objects of the present invention are also solved by the use of an emulsion as defined above in a pharmaceutical formulation, a cosmetic or personal care product or a food product.

The objects of the present invention are also solved by a pharmaceutical formulation comprising an emulsion as defined above. In one embodiment, said pharmaceutical formulation is a controlled or sustained release pharmaceutical formulation. In one embodiment, the pharmaceutical composition further comprises a bioactive agent as defined above. In one embodiment, the pharmaceutical composition further comprises a pharmaceutically acceptable carrier. In one embodiment, the pharmaceutical composition is applied topically.

The objects of the present invention are also solved by a cosmetic or personal care product comprising an emulsion as defined above. In one embodiment, the cosmetic product is applied topically.

The objects of the present invention are also solved by a food product comprising an emulsion as defined above.

The present invention provides a simple and low-cost technology to formulate organogels or emulsion. The technology involves simply dissolving the above defined ultrasmall self-assembling peptides (preferably dimers to hexamers) acting as low molecular weight (LMW) gelators/emulsifiers in organic solutions (up to 99.9% organic solvent or 98% oil). These organic solutions include organic solvents, oils or solvent mixtures such as oil-organic solvent, oil-aqueous or oil-aqueous-organic solvents. The inventors screened different solvents from polar to non-polar solvents, such as methanol and hexane. Optimization of peptide organogels for various applications can be achieved by tuning the combinations and ratios of peptides and solvent systems, in particular by tuning the concentration of the peptides.

The peptides used in accordance with the present invention not only self-assemble, but also can interact with complex macromolecular structures. Thus, they are able to facilitate the design and development of technologies involving synthetic and biological systems.

The organogels formed from peptides are stabilized due to the weak interactions between the peptide aggregates and solvent systems. These include interactions such as hydrophobic, non-covalent bondings, van der Waals, electrostatic, hydrogen bonding and/or π-π interactions (in the case of peptides having an aromatic head group), etc. The properties of the peptide gelators such as polarity, size and thermo reversibility also play a key role in the formulation of organogels. The peptides are also biocompatible, which can be used for formulating the organogels for biological applications.

The peptides can entrap up to 99.9% of organic solvents. The inventors also found that these peptide organogels could successfully immobilize quantum dots (QDs). Furthermore, fluorescent measurement studies on QD-loaded peptide organogels showed a complete overlap of emission peaks with that of QDs in solution. This indicates that the QDs were stable in the peptide organogels. The peptide organogels have a high organic solvent content and can immobilize all kinds of inorganic and organic materials. Thus, this technology can be further used, besides biomedical applications, for the development of devices, sensors or substrates in the electronic and chemical industries.

The peptides disclosed herein also form organogels in lipophilic solvent systems (e.g. oil, up to 98%), indicating the versatility of these peptides as organogelators. Oil-based peptide organogels are stable and possess high mechanical strength and can be used for encapsulating hydrophobic therapeutic or non-therapeutic materials. For example; the active pharmaceutical ingredients loaded in peptide organogels can be clinically used as topical, oral, implantable or parenteral delivery systems. Furthermore, peptide organogels based on herbal, edible and/or essential oils allow for the use of these systems in the fields of cosmetics, food and pharmaceutical technologies. Thus, depending on the material immobilized by the peptide organogels, they can be used for both biological and non-biological applications.

Since some of the peptides disclosed herein are amphiphilic, they emulsify the solvent mixture of aqueous and organic phases to form stable gel or emulsion systems. Therefore, addition of an aqueous and organic phase in the presence of ultrasmall peptides facilitates the formation of stable emulsions, microgels or particulate delivery systems. These delivery systems can be used for both hydrophilic and hydrophobic materials. For example, the inventors found that such peptide emulsion systems could encapsulate dyes. Hence, the peptide gelators/emulsifiers used in accordance with the present invention can be utilized to formulate particulate- and emulsion-based technologies for therapeutic and non-therapeutic applications.

In summary, the present invention provides a straightforward and cost-efficient technology for formulating various types of organogels or emulsions in different solvent phase systems in the presence of specific ultrasmall peptide gelators/emulsifiers (preferably dimers to hexamers). Furthermore, these peptide organogels can be used for encapsulating both hydrophilic and hydrophobic materials for biological and non-biological applications. For example, they can be used as delivery systems for bioactive agents immobilized therein. The tailored release of the bioactive agents from these delivery systems could be achieved by modulating the solvent systems and peptide properties. The peptide gelators/emulsifiers may also be conjugated to polymers, dendrimers, inorganic, organic, therapeutic and/or non-therapeutic materials for various applications.

BRIEF DESCRIPTION OF THE DRAWINGS

Reference is now made to the figures, wherein.

EXAMPLES

Reference is now made to the following examples, which are meant to illustrate the present invention and not to limit it:

Ultrasmall Peptide Organogel Based on Organic Solvents

Figure 1:
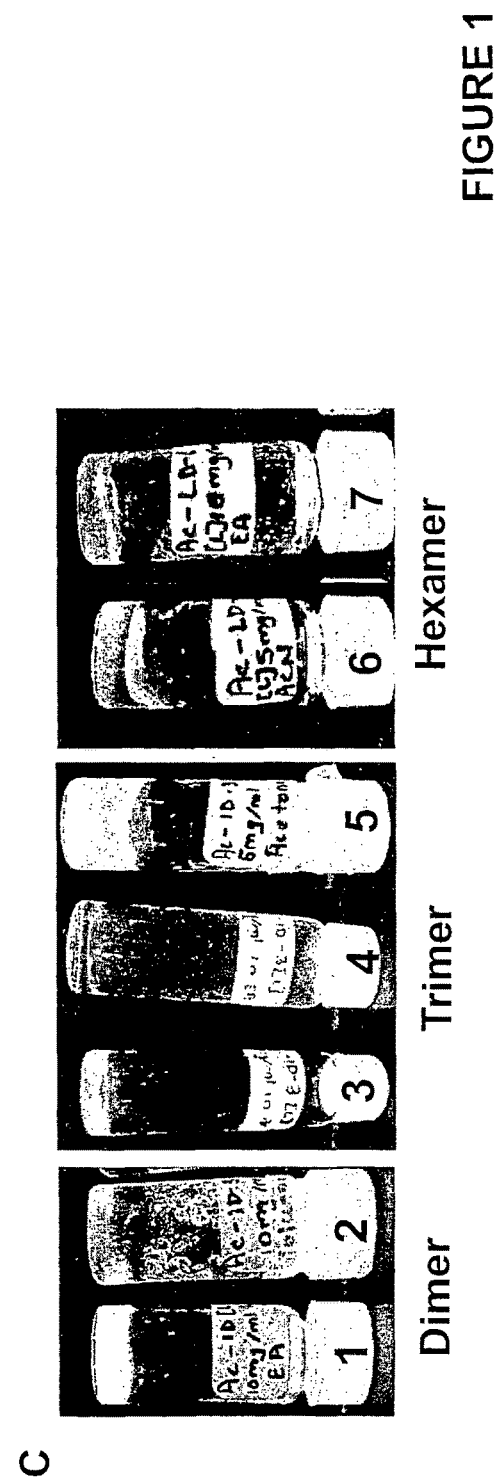
FIG. 1 shows the formulation of organogels with peptides having a polar amino acid head group in different organic solvents (A/B). The exemplary peptides are Ac-ID-COOH (L) (dimer), Ac-IVD-COOH (L) (trimer) and Ac-LIVAGD-COOH (L) (hexamer). The organogels depicted in (C) are (1) Ac-ID-COOH (L) 10 mg/ml in ethyl acetate, (2) Ac-ID-COOH (L) 10 mg/ml in toluene, (3) Ac-IVD-COOH (L) 2 mg/ml in acetonitrile, (4) Ac-IVD-COOH (L) 2 mg/ml in ethyl acetate, (5) Ac-IVD-COOH (L) 5 mg/ml in acetone, (6) Ac-LIVAGD-COOH (L) 5 mg/ml in toluene, and (7) Ac-LIVAGD-COOH (L) 10 mg/ml in ethyl acetate.
Figure 1:
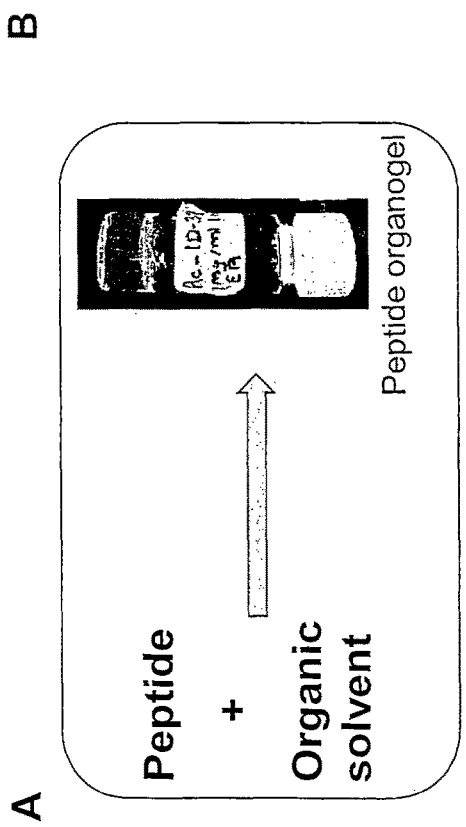
Figure 2:
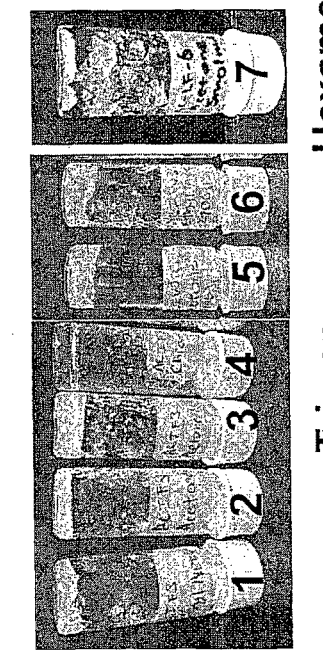
FIG. 2A shows the formulation of organogels with peptides having an aromatic amino acid head group in different organic solvents (peptide concentration 0.5% w/v). The organogels depicted in (B) are (1) Ac-IVF-COOH (L) 5 mg/ml in ethyl acetate, (2) Ac-IVF-COOH (L) 5 mg/ml in acetone, (3) Ac-IVF-COOH (L) 5 mg/ml in acetonitrile, (4) Ac-IVF-COOH (L) 5 mg/ml in chloroform, (5) Ac-IVW-COOH (L) 5 mg/ml in acetone, (6) Ac-IVW-COOH (L) 5 mg/ml in ethyl acetate, and (7) Ac-LIVAGF-COOH (L) 5 mg/ml in acetone.

Ultrasmall peptides with a polar head group, such as Ac-LIVAGD-COOH (L) and Ac-IVD-COOH (L), or an aromatic head group, such as Ac-IVF-COOH (L) and Ac-IVW-COOH (L) formed organogels in organic solvents (see FIGS. 1 and 2 as well as Table 1). The resulting organogels showed visible changes in their appearance when altering the peptide concentrations (FIGS. 3A and 3B) and the organic solvents.

Figure 3:
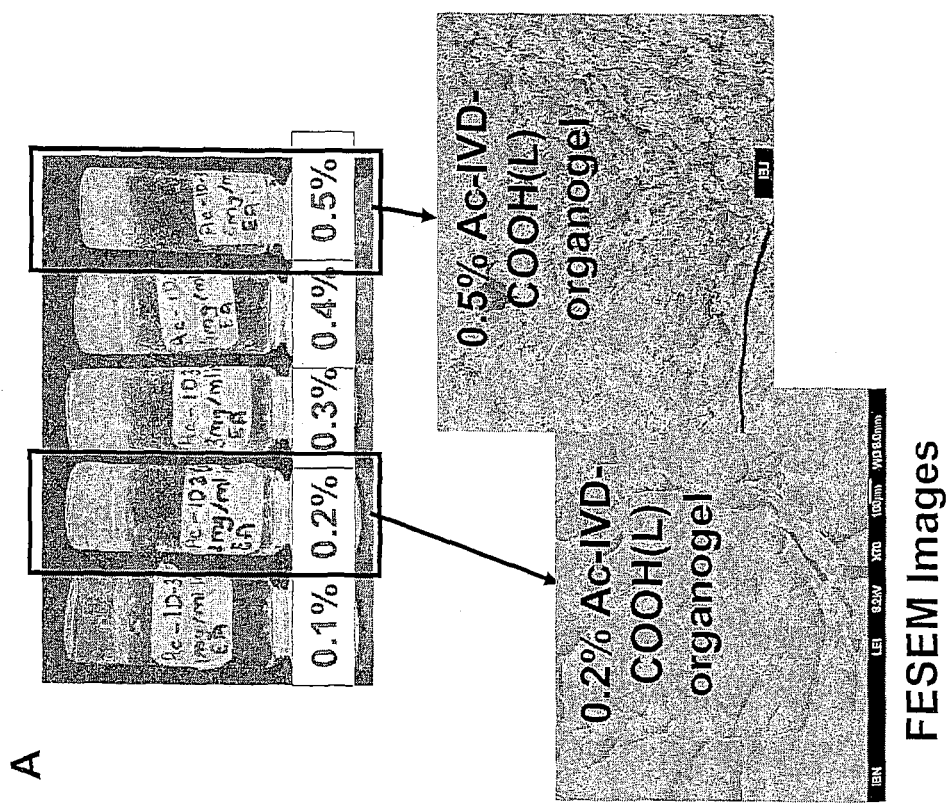
FIG. 3A shows the effect of the peptide concentration on organogelation for the trimer Ac-IVD-COOH (L) in ethyl acetate. Gels with increasing concentration of Ac-IVD-COOH (L) were prepared in ethyl acetate. For concentrations above 10 mg/ml (1% w/v) only partial gelation was observed. Organogels of 2 mg/ml and 5 mg/ml Ac-IVD-COOH (L) in ethyl acetate were analyzed by field emission scanning electron microscopy (FESEM).
FIGS. 3B and 3C show the effect of the peptide concentration on organogelation for the hexamer Ac-LIVAGD-COOH (L) in acetonitrile or ethyl acetate. Increasing the concentration of Ac-LIVAGD-COOH (L) in acetonitrile (1 mg/ml, 2 mg/ml, 3 mg/ml, 4 mg/ml, 5 mg/ml, 10 mg/ml, 20 mg/ml; from left to right) resulted in an increased size of the organogel (B). Increasing the concentration of Ac-LIVAGD-COOH (L) in ethyl acetate (5 mg/ml, 10 mg/ml, 20 mg/ml; from left to right) resulted in partial gelation (C).
Figure 3:
Figure 3:

The formulation of the peptide organogels depends on several factors, such as peptide concentration, polarity of the organic solvent, peptide sequence and type of solvent used (see FIG. 3 as well as FIGS. 10A-G and 11). For example, increasing the peptide concentration reduced the gelation time for the formulation of peptide organogels. Based on the experimental data disclosed herein and his general knowledge, a person skilled in the art would have no problems in figuring out suitable gelation conditions (e.g. a suitable organic solvent) for a given peptide. For example, a skilled person knows about the nature of an organic solvent with respect to its polarity or non-polarity. As can be seen from FIG. 1B, in particular polar solvents with a carbonyl-, nitrile- or benzene-group that, preferably, are not too bulky in size will not interfere with organogelation. Obviously, there is interaction with the polar head group of the peptide. Interference of the solvent with the hydrophobic tail of the peptide would likely hinder or slow down gel formation, as can be seen with the hydrophobic solvent hexane. Also, it seems that planar configurations (benzene ring, C=O, nitrile) within the solvent helps to stabilize the gel. This might be explained with a more favourable interaction of p-, $sp^2$-, or sp-orbitals.

Figure 4:
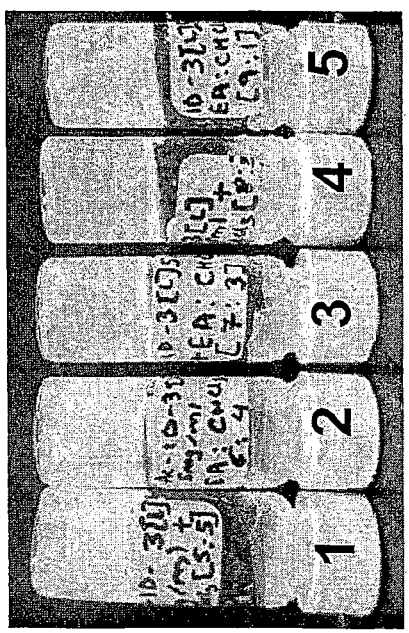
FIG. 4 shows the screening for organogels that are suitable for loading with quantum dots. Since the CdS—CdSe—ZnS quantum dots used are soluble in chloroform, while Ac-IVD-COOH (L) gelled preferably in ethyl acetate, solvent mixtures of ethyl acetate:chloroform were screened. Gels of 5 mg/ml Ac-IVD-COOH (L) in different mixtures of ethyl acetate:chloroform were prepared. Peptide organogels with an 8:2 mixture of ethyl acetate:chloroform were selected for quantum dot loading.
Figure 5:
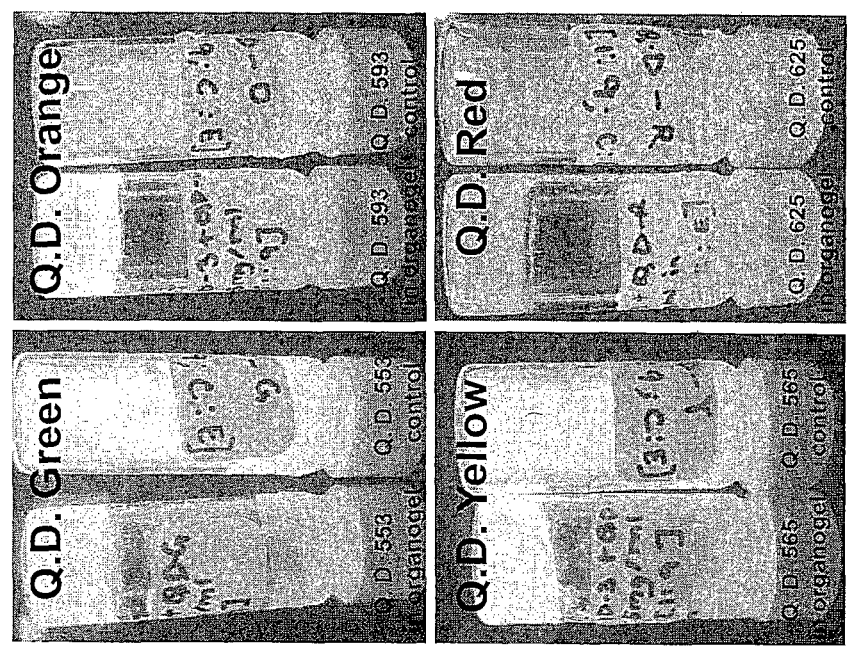
FIGS. 5A and B shows the fluorescence of organogels loaded with four different-sized CdS—CdSe—ZnS quantum dots (Q.D.) upon 480 nm excitation. The organogels were based on 5 mg/ml Ac-IVD-COOH (L) in an 8:2 mixture of ethyl acetate:chloroform. The quantum dots were used at a concentration of 0.2 mg/ml.
Figure 5:
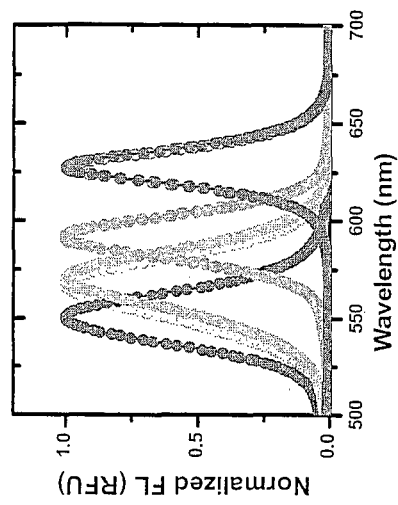

Materials, such as quantum dots (as seen in FIGS. 4 and 5), or metal nanoparticles (e.g. gold nanoparticles), can be incorporated in the peptide organogels by encapsulation, immobilization (in the bulk phase) or conjugation to the peptide gelators. Thus, the peptide organogels can be used in the design and development of sensors and (other) electronic devices.

Ultrasmall Peptide Organogels Based on Lipophilic (Oil) and Organic Solvent-Lipophilic Systems/Ultrasmall Peptide Emulsions Based on Lipophilic-Aqueous and Organic Solvent-Lipophilic-Aqueous Systems Ultrasmall peptides formed organogels and emulsions in oil and oil-based solvent mixtures (see FIGS. 6 to 8 and 10H as well as Table 1). The formation of lipophilic solvent-based peptide organogels and emulsions depend on several factors, such as peptide concentration, type of oil, ratio of solvent and oil, peptide sequence, peptide size, and formulation technique such as heating, sonication or use of cosolvents. Based on the experimental data disclosed herein and his general knowledge, a person skilled in the art would have no problems in figuring out suitable gelation or emulsifying conditions (e.g. a suitable solvent system) for a given peptide.

Figure 6:
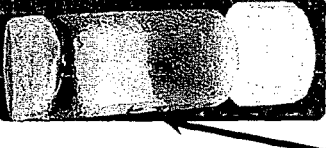
FIG. 6 shows the formulation of organogels with peptides in oils. Different concentrations of the trimer Ac-IVD-COOH (L) were screened for organogelation in sunflower oil (A). The rheological properties of the resulting organogel were studied by oscillation frequency sweep analysis (geometry: 8 mm serrated parallel plate; strain: 0.1%; transducer mode: FRT; N=1) (B).
Figure 6:
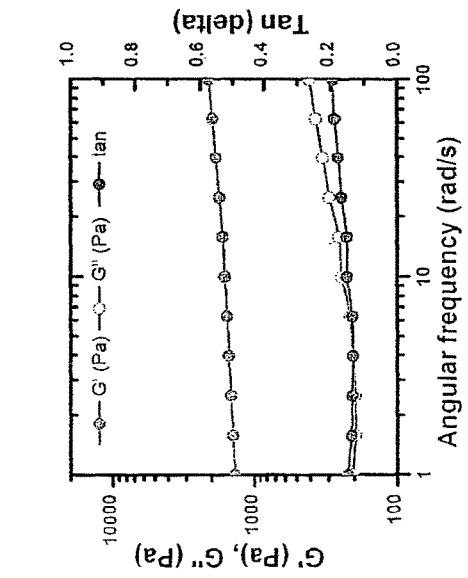
Figure 7:
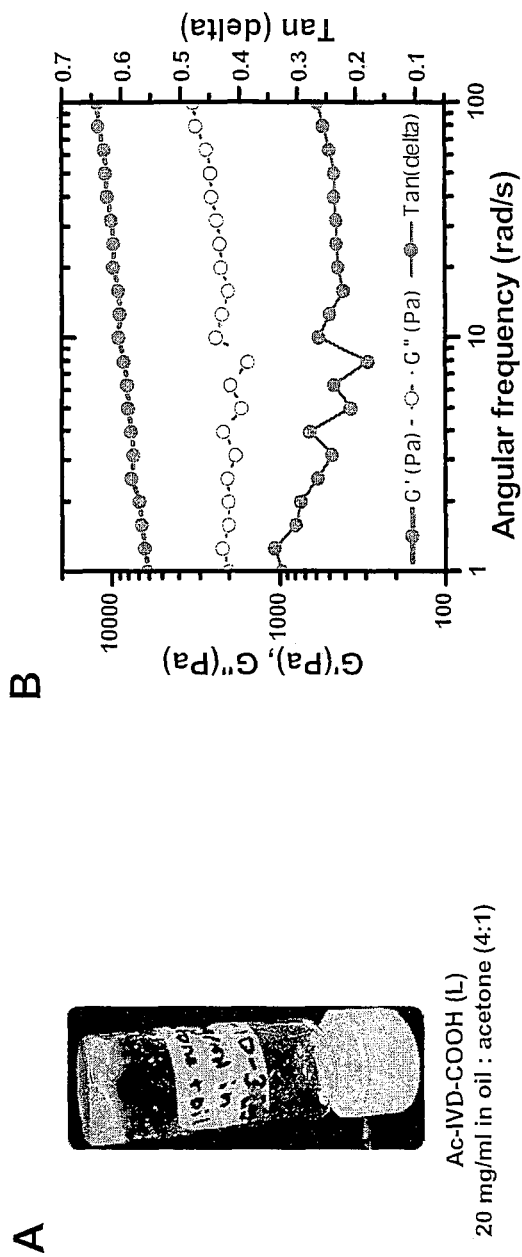
FIG. 7 shows the formulation of peptide organogels in oil:solvent mixtures. An organogel of 20 mg/ml Ac-IVD-COOH (L) in sunflower oil:acetone (4:1) was prepared (A). The rheological properties of the resulting organogel were studied by oscillation frequency sweep analysis (geometry: 8 mm serrated parallel plate; strain: 0.1%; transducer mode: FRT) (B).
Figure 8:
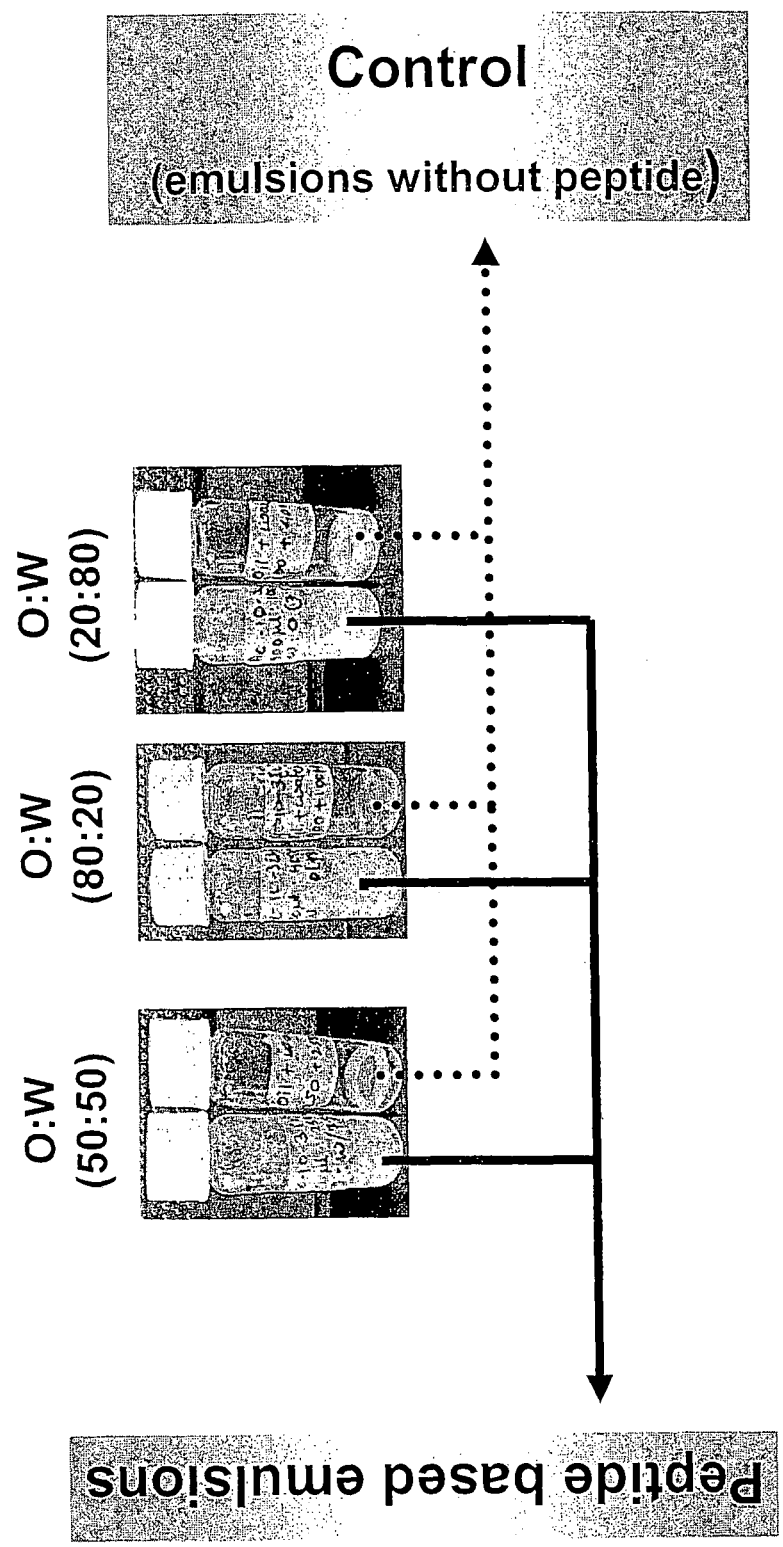
FIG. 8 shows the formulation of stable peptide emulsions in solvent mixtures of oil (O) and water (W). 7.5 mg/ml Ac-IVD-COOH (L) were dissolved in solvent mixtures of oil:water (50:50, 80:20, 20:80). No phase separation was observed in the peptide-based formulations in comparison to controls.

Rheology studies showed that the organogels possess good mechanical properties, since the Tan(G"/G') is less than 1 (~0.2-0.3), with a storage modulus (G') of 1100 Pa and 10050 Pa for organogels based on oil and oil/solvent mixtures, respectively, and a loss modulus (G") of 120 Pa and 1200 Pa for organogels based on oil and oil/solvent mixtures, respectively (FIGS. 6 and 7).

Figure 9:
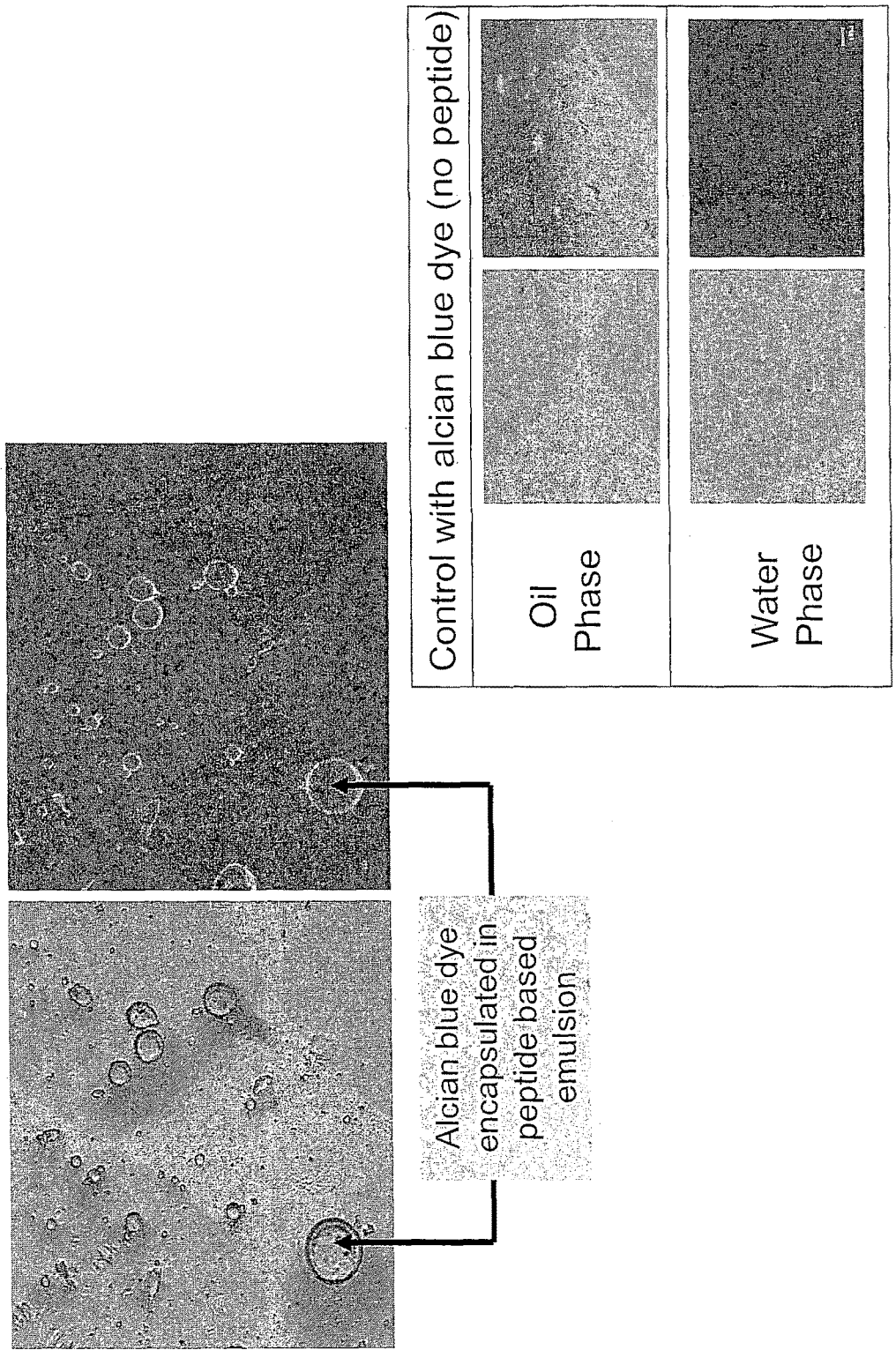
FIG. 9 shows the loading of an Ac-IVD-COOH (L) emulsion (water:oil—40:60) with Alcian blue dye.
Figure 10:
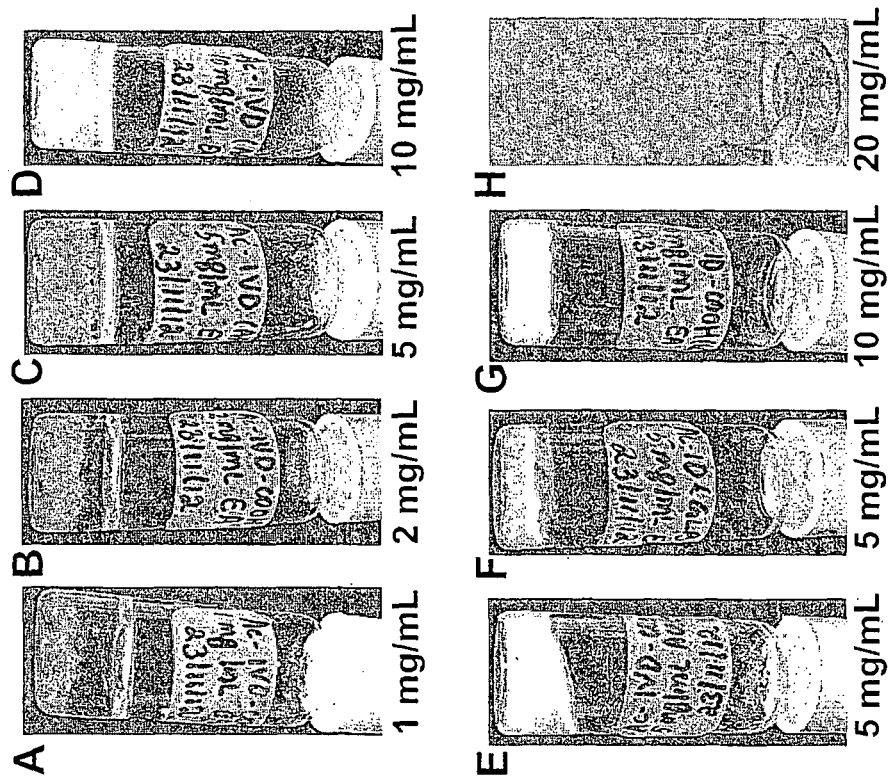
FIG. 10 shows organogels from dimer and trimer peptides. (A-D) Ac-IVD-COOH (L) in ethyl acetate at a concentration of 1, 2, 5 and 10 mg/ml, respectively. (E) Ac-IVD-COOH (L) in acetone at 5 mg/ml concentration. (F-G) Ac-ID-COOH (L) in ethyl acetate at 5 and 10 mg/ml concentration. (H) Ac-ID-COOH (L) in vegetable oil at 20 mg/ml concentration.
Figure 11:
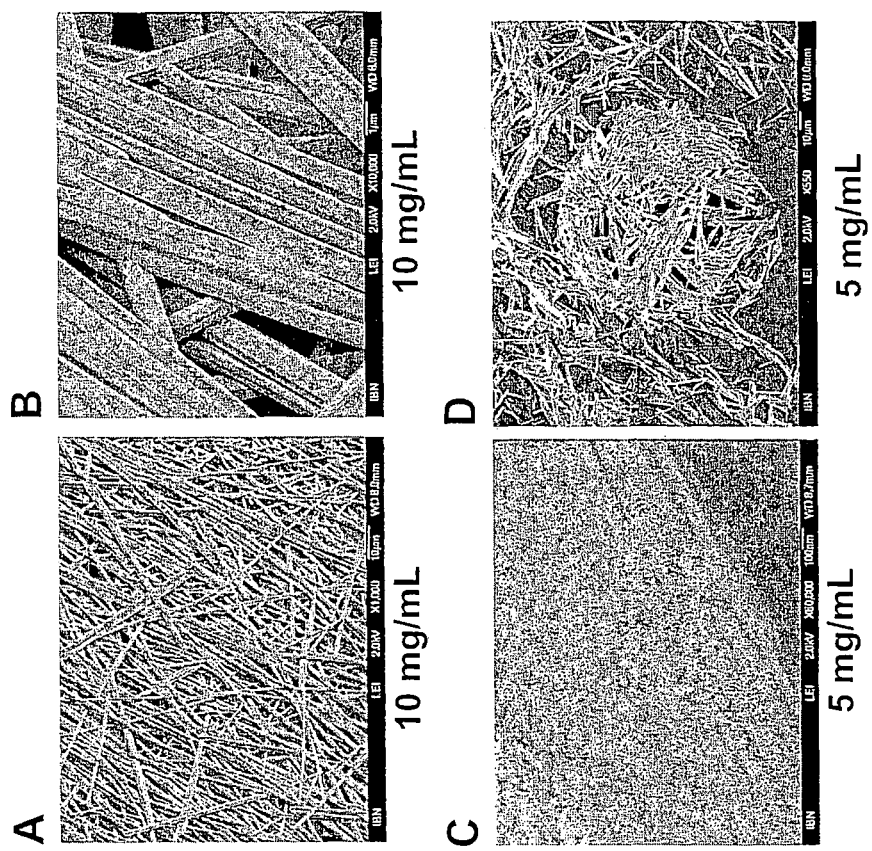
FIG. 11 shows the morphological characterization of organogels formed by the dimer Ac-ID-COOH (L) by field emission scanning electron microscopy (FESEM). (A-B) 10 mg/ml in ethyl acetate at 1000× and 10,000×, respectively. (C) 5 mg/ml in ethyl acetate at 60,000×. (D) 5 mg/ml in water at 550×.

Bioactive agents/therapeutics, such as prodrugs and drugs, excipients, dyes (see FIG. 9), pigments, inorganic and organic materials can be incorporated into the peptide based organogels, emulsions or particulate delivery systems for biological or non-biological applications. This can be achieved by encapsulation, immobilization (in the bulk phase) or conjugation to the peptide organogelators/emulsifiers. The gels and emulsions can be subsequently used in pharmaceutical, cosmetic and food technologies.

TABLE 1

Exemplary peptides forming organogels and/or emulsions

| SEQ ID NO. | Peptide Sequence | Description |
|---|---|---|
| Peptides forming organogels in organic solvents | | |
| 44 | Ac-ID-COOH (L) | dimer/polar amino acid head group |
| 30 | Ac-IVD-COOH (L) | trimer/polar amino acid head group |
| 11 | Ac-LIVAGD-COOH (L) | hexamer/polar amino acid head group |
| 32 | Ac-IVW-COOH (L) | trimer/aromatic amino acid head group |
| 31 | Ac-IVF-COOH (L) | trimer/aromatic amino acid head group |
| 12 | Ac-LIVAGF-COOH (L) | hexamer/aromatic amino acid head group |
| Peptides forming organogels in mixtures of oils and other organic solvents | | |
| 30 | Ac-IVD-COOH (L) | trimer/polar amino acid head group |
| Peptides forming emulsions in solvent mixtures (water:oil or org.solv.:water:oil) | | |
| 30 | Ac-IVD-COOH (L) | trimer/polar amino acid head group |
| 11 | Ac-LIVAGD-COOH (L) | hexamer/polar amino acid head group |

The features of the present invention disclosed in the specification, the claims, and/or in the accompanying drawings may, both separately and in any combination thereof, be material for realizing the invention in various forms thereof.

The invention claimed is:

1. An organogel comprising
an organic solvent and
a peptide having the general formula $$Z-(X)_a\text{-}(Y)_b-Z'_c,$$

wherein
Z is an N-terminal protecting group consisting of an acetyl group;
$(X)_a-(Y)_b$ has a sequence selected from the group consisting of LIVAGD (SEQ ID NO: 11), IVD (SEQ ID NO: 30), IVF (SEQ ID NO: 31), IVW (SEQ ID NO: 32), and ID (SEQ ID NO: 44);
Z'c is a C-terminal protecting group consisting of a carboxyl group;
wherein the organic solvent is selected from the group consisting of ethyl acetate, chloroform, sunflower oil and mixtures thereof; and
wherein when $(X)_a-(Y)_b$ has an amino acid sequence selected from the group consisting of LIVAGD (SEQ ID NO: 11), IVD (SEQ ID NO: 30), IVF (SEQ ID NO: 31), IVW (SEQ ID NO: 32), and ID (SEQ ID NO: 44), the organic solvent comprises ethyl acetate; or
when $(X)_a-(Y)_b$ has a sequence consisting of IVF (SEQ ID NO: 31), the organic solvent comprises chloroform; or
when $(X)_a-(Y)_b$ has a sequence selected from the group consisting of IVD (SEQ ID NO: 30), and ID (SEQ ID NO: 44), the organic solvent comprises sunflower oil; or when $(X)_a$—$(Y)_b$ has a sequence IVD (SEQ ID NO: 30), the organic solvent comprises a mixture of ethyl acetate and chloroform.

2. The organogel according to claim 1, wherein said peptide is present at a concentration in the range of from 0.1% to 30% (w/w), with respect to the total weight of said organogel, and/or wherein said organogel has a tan d of less than 1.

3. The organogel according to claim 1, further comprising at least one additional substance, wherein said at least one additional substance is encapsulated by said organogel, immobilized in the bulk phase of said organogel or conjugated to said peptide,
and/or wherein said at least one additional substance is a bioactive agent,
or wherein said at least one additional substance is selected from the group consisting of dyes, pigments, quantum dot nanoparticles and other nanoparticles.

4. A method of producing the organogels of claim 1, said method comprising the step of dissolving the peptide in an organic solvent, wherein the organic solvent is selected from the group consisting of ethyl acetate, chloroform, sunflower oil, or a mixture of ethyl acetate and chloroform.

5. A pharmaceutical formulation comprising the organogel of claim 1.

6. A cosmetic or personal care product comprising the organogel of claim 1, or a food product comprising the organogel of claim 1, or a device comprising the organogel of claim 1, wherein said device is a sensor device and/or is an electronic device.

7. An emulsion comprising
an organic solvent,
a polar solvent, wherein the polar solvent is an aqueous solution, and
a peptide having the general formula

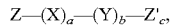
Z—$(X)_a$—$(Y)_b$—$Z'_c$, wherein
Z is an N-terminal protecting group consisting of an acetyl group;
$(X)a$-$(Y)b$ has a sequence selected from the group consisting of LIVAGD (SEQ ID NO: 11), IVD (SEQ ID NO: 30), IVF (SEQ ID NO: 31), IVW (SEQ ID NO: 32), and ID (SEQ ID NO: 44)
Z' is a C-terminal protecting group consisting of a carboxyl group;
and
wherein when $(X)_a$—$(Y)_b$ has an amino acid sequence selected from the group consisting of LIVAGD (SEQ ID NO: 11), IVD (SEQ ID NO: 30), IVF (SEQ ID NO: 31), IVW (SEQ ID NO: 32), and ID (SEQ ID NO: 44), the organic solvent comprises ethyl acetate; or
when $(X)_a$—$(Y)_b$ has a sequence consisting of IVF (SEQ ID NO: 31), the organic solvent comprises chloroform; or
$(X)$, —$(Y)b$ has a sequence selected from the group consisting of IVD (SEQ ID NO: 30), and ID (SEQ ID NO: 44), the organic solvent comprises sunflower oil; or
when $(X)_a$—$(Y)_b$ has a sequence IVD (SEQ ID NO: 30), the organic solvent comprises a mixture of ethyl acetate and chloroform.

8. The emulsion according to claim 7, wherein said N-terminal protecting group has the general formula C(O)—R, wherein R is selected from the group consisting of H, alkyl and substituted alkyl, wherein the alkyl is selected from the group consisting of methyl, ethyl, propyl, isopropyl, butyl and isobutyl, and/or wherein said N-terminal protecting group is an acetyl group.

9. The organogel according to claim 3, wherein said bioactive agent is selected from the group consisting of nucleic acids, (poly)peptides, virus particles, oligosaccharides, polysaccharides, vitamins, sialic acids, antigens, vaccines, drugs, prodrugs, and other organic or inorganic bioactive compounds.

10. The organogel according to claim 3, wherein said other nanoparticles are metal or semiconductor nanoparticles.

11. The pharmaceutical formulation according to claim 5, wherein said pharmaceutical formulation is a controlled or sustained release pharmaceutical formulation.

* * * * *